United States Patent
Toyooka (10) Patent No.: US 10,188,267 B2
(45) Date of Patent: Jan. 29, 2019

(54) DISTAL END STRUCTURE OF ENDOSCOPE

(71) Applicant: OLYMPUS CORPORATION, Tokyo (JP)

(72) Inventor: Takuya Toyooka, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 149 days.

(21) Appl. No.: 15/342,702

(22) Filed: Nov. 3, 2016

(65) Prior Publication Data
US 2017/0049300 A1 Feb. 23, 2017

Related U.S. Application Data

(63) Continuation of application No. PCT/JP2015/063772, filed on May 13, 2015.

(30) Foreign Application Priority Data

Sep. 4, 2014 (JP) ................. 2014-180586

(51) Int. Cl.
*A61B 1/00* (2006.01)
*A61B 1/018* (2006.01)
*G02B 23/24* (2006.01)

(52) U.S. Cl.
CPC ........ *A61B 1/00098* (2013.01); *A61B 1/0008* (2013.01); *A61B 1/00087* (2013.01);
(Continued)

(58) Field of Classification Search
CPC .............. A61B 1/0008; A61B 1/00089; A61B 1/00101; A61B 1/00098
(Continued)

(56) References Cited

U.S. PATENT DOCUMENTS 5,860,913 A * 1/1999 Yamaya ............ A61B 1/00091
600/121
6,605,033 B1 * 8/2003 Matsuno ............ A61B 1/00098
600/106
(Continued)

FOREIGN PATENT DOCUMENTS

EP 2436300 A1 4/2012
JP 2002-034905 A 2/2002
(Continued)

OTHER PUBLICATIONS

International Search Report dated Aug. 11, 2015 issued in PCT/JP2015/063772.

*Primary Examiner* — Matthew J Kasztejna
(74) *Attorney, Agent, or Firm* — Scully, Scott, Murphy & Presser, P.C.

(57) ABSTRACT

A distal end structure of an endoscope includes: an opening of a treatment instrument insertion channel formed on a distal end of an insertion portion in the endoscope and including an opening having a long side and a short side; a first wall portion extending in a longitudinal direction so as to face the opening, at the distal end; and a second wall portion facing the first wall portion in a short side direction so as to sandwich the opening and extending in the long side direction, at the distal end, wherein a first end surface in the first wall portion and a second end surface in the second wall portion are inclined such that inclination directions in the longitudinal axis direction are opposite to each other.

9 Claims, 8 Drawing Sheets

(52) U.S. Cl.
CPC ...... *A61B 1/00089* (2013.01); *A61B 1/00096* (2013.01); *A61B 1/00101* (2013.01); *A61B 1/018* (2013.01); *G02B 23/2423* (2013.01)

(58) Field of Classification Search
USPC .................................................. 600/127, 129
See application file for complete search history.

(56) References Cited

U.S. PATENT DOCUMENTS

| | | | | |
|---|---|---|---|---|
| 6,695,764 B2* | 2/2004 | Silverman | ................. | A61F 2/04 600/29 |
| 6,755,782 B2* | 6/2004 | Ogawa | ............... | A61B 1/00087 600/127 |
| 7,766,819 B2* | 8/2010 | Matsumoto | ........ | A61B 1/00089 600/128 |
| 8,075,478 B2* | 12/2011 | Campos | ............... | A61B 1/0008 600/111 |
| 9,072,443 B2* | 7/2015 | Hashido | ............. | A61B 1/00089 |
| 9,913,574 B2* | 3/2018 | Surti | ....................... | A61B 1/012 |
| 2002/0091303 A1 | 7/2002 | Ootawara et al. | | |
| 2004/0127767 A1* | 7/2004 | Fleener | ............... | A61B 1/00087 600/127 |
| 2005/0043584 A1* | 2/2005 | Nozue | ................ | A61B 1/00089 600/127 |
| 2005/0165272 A1* | 7/2005 | Okada | .................. | A61B 1/0008 600/114 |
| 2005/0165419 A1* | 7/2005 | Sauer | ................... | A61B 1/0014 606/148 |
| 2011/0313242 A1* | 12/2011 | Surti | .................. | A61B 1/00089 600/104 |
| 2015/0157189 A1* | 6/2015 | Shimada | ............ | A61B 1/00071 600/137 |

FOREIGN PATENT DOCUMENTS

| | | |
|---|---|---|
| JP | 2002-253484 A | 9/2002 |
| JP | 2010-253069 A | 11/2010 |
| JP | 2012-075658 A | 4/2012 |
| WO | WO 2001/078581 | 10/2001 |

\* cited by examiner

DISTAL END STRUCTURE OF ENDOSCOPE

CROSS REFERENCE TO RELATED APPLICATION

This application is a continuation application of PCT/JP2015/063772 filed on May 13, 2015 and claims benefit of Japanese Application No. 2014-180586 filed in Japan on Sep. 4, 2014, the entire contents of which are incorporated herein by this reference.

BACKGROUND OF THE INVENTION

1. Field of the Invention

The present invention relates to a distal end structure of an endoscope including an opening of a treatment instrument insertion channel on a distal end of an insertion portion of the endoscope.

2. Description of the Related Art

In recent years, an endoscope has been widely used in a medical field and an industrial field. The endoscope can observe inside of a subject by inserting an elongated insertion portion into a subject.

Note that an example of a well-known endoscope includes an already-known front-view type endoscope provided with an observation lens, an illumination lens, an opening of a treatment instrument insertion channel (hereinafter, called channel opening) on a distal end surface of a distal end portion provided on a distal end side of an insertion portion in a longitudinal axis direction (hereinafter, simply called distal end side), the endoscope observing and treating a site to be examined in front of the distal end surface in the longitudinal axis direction (hereinafter, simply called front) in the subject.

As shown in Japanese Patent Application Laid-Open Publication No. 2010-253069, another example of a well-known endoscope includes an already-known side-view type endoscope provided with an observation lens, an illumination lens, and a channel opening on part of a peripheral surface of a distal end portion of an insertion portion, the endoscope observing and treating a site to be examined on a lateral side with respect to the longitudinal axis direction in the subject.

Here, a technique is well-known, in which a medical side-view type endoscope as disclosed for example in Japanese Patent Application Laid-Open Publication No. 2010-253069 is used, and an already-known elongated stent placed in, for example, a bile duct and configured to expand the diameter of a stenosis of the bile duct is recovered through the opening of the treatment instrument insertion channel.

Specifically, in the technique, an already-known recovery treatment instrument, such as a snare and grasping forceps, is first inserted into the treatment instrument insertion channel from an operation portion side of the endoscope, and a distal end side of the recovery treatment instrument is projected from the channel opening.

Subsequently, the stent is held on the distal end side of the recovery treatment instrument, and lastly, the stent is drawn into the treatment instrument insertion channel along with the recovery treatment instrument through the channel opening to recover the stent.

Note that at the recovery, the stent is delivered across the channel opening in the bile duct. In a state that the distal end side of the recovery treatment instrument holds near the center of the stent, drawing force in drawing the recovery treatment instrument and each opening edge portion of the channel opening are used to draw the stent into the treatment instrument insertion channel through the channel opening while the stent is folded in half near the center.

SUMMARY OF THE INVENTION

An aspect of the present invention provides a distal end structure of an endoscope including: an opening of a treatment instrument insertion channel formed on a distal end of an insertion portion in the endoscope and including an opening having a long side and a short side; a first wall portion extending in a long side direction having the long side so as to face the opening, at the distal end of the insertion portion; and a second wall portion facing the first wall portion in a short side direction having the short side so as to sandwich the opening and extending in the long side direction, at the distal end of the insertion portion, wherein a first end surface of a top portion in the first wall portion and a second end surface of a top portion in the second wall portion are inclined such that inclination directions in the long side direction are opposite to each other.

DETAILED DESCRIPTION OF THE PREFERRED EMBODIMENT(S)

Hereinafter, an embodiment of the present invention will be described with reference to the drawings. Note that the drawings are schematic drawings, and a relationship between a thickness and a width of each member, a ratio of the thickness of respective members, and the like are different from the reality. It is obvious that the relationship and the ratio of dimensions between the drawings are different in some parts of the drawings.

Note that a side-view type endoscope will be described below as an example of an endoscope. A stent will be described as an example of an elongated matter to be recovered by using the side-view type endoscope, and a snare will be described as an example of a recovery treatment instrument used for recovering the stent.

Figure 1:
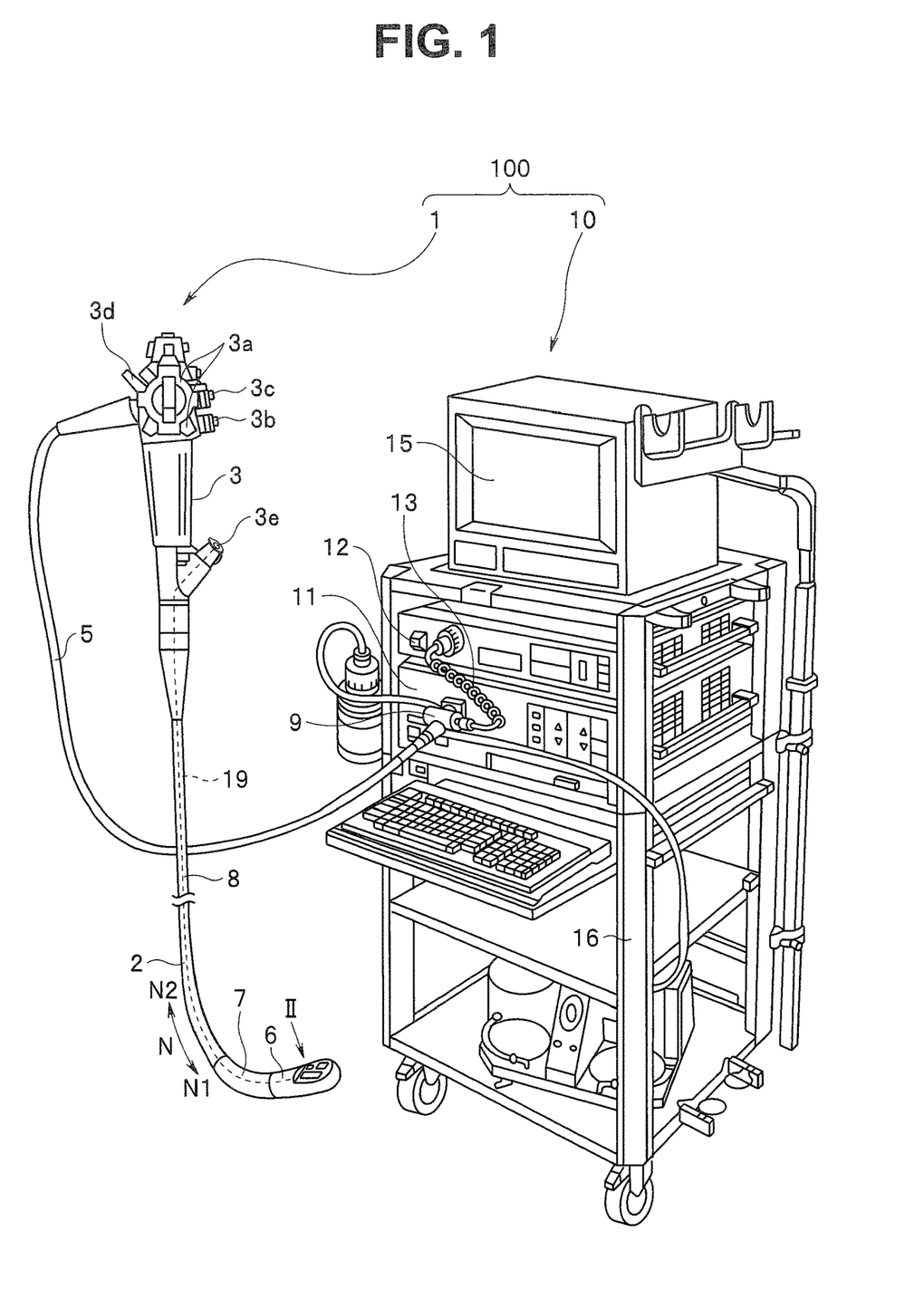
FIG. 1 is a perspective view schematically showing an example of an endoscope apparatus including an endoscope with a distal end structure of the present embodiment and a peripheral apparatus.

FIG. 1 is a perspective view schematically showing an example of an endoscope apparatus including an endoscope with a distal end structure of the present embodiment and a peripheral apparatus.

As shown in FIG. 1, main parts of an endoscope apparatus 100 include an endoscope 1 and a peripheral apparatus 10.

Main parts of the endoscope 1 include: an insertion portion 2 inserted into a subject; an operation portion 3 consecutively connected to a proximal end of the insertion portion 2 in a longitudinal axis direction N (hereinafter, simply called a proximal end); a universal cord 5 extended from the operation portion 3; and a connector 9 provided on an extension end of the universal cord 5.

The peripheral apparatus 10 includes a light source apparatus 11, a video processor 12, a connection cable 13 for electrically connecting the light source apparatus 11 and the video processor 12, and a monitor 15, which are placed on a stand 16.

The endoscope 1 and the peripheral apparatus 10 configured in this way are connected to each other through the connector 9. The connector 9 is connected to, for example, the light source apparatus 11 of the peripheral apparatus 10.

A bending operation knob 3a, an air/water feeding operation button 3b, a suction operation button 3c, and a raising base operation knob 3d are provided on the operation portion 3 of the endoscope 1.

Note that the raising base operation knob 3d is a knob for inputting operation of raising or lowering a treatment instrument raising base not shown positioned to face a channel opening 25 (see FIG. 2) described later in a treatment instrument insertion channel 19 provided in the insertion portion 2.

A treatment instrument insertion port 3e for inserting various treatment instruments and a snare 60 described later into the treatment instrument insertion channel 19 from outside of the operation portion 3 is also provided on the operation portion 3.

The insertion portion 2 includes: a distal end portion 6 positioned on a distal end side of the insertion portion 2; a bending portion 7 consecutively connected to a proximal end of the distal end portion 6; and a flexible tube portion 8 consecutively connected to a proximal end of the bending portion 7.

The bending portion 7 is bent and operated in, for example, four vertical and horizontal directions by using the bending operation knob 3a provided on the operation portion 3.

Figure 2:
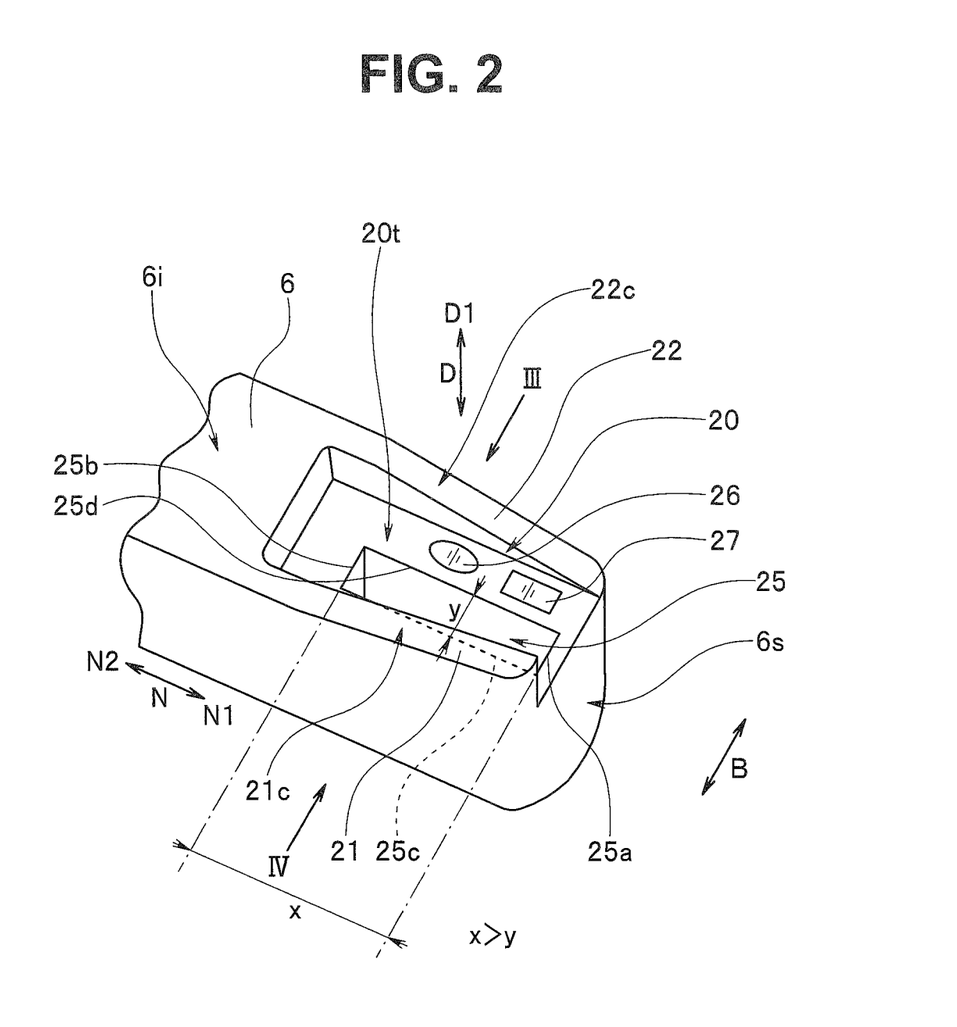
FIG. 2 is an enlarged perspective view schematically viewing a distal end portion of an insertion portion of FIG. 1 in a direction II in FIG. 1.
Figure 3:
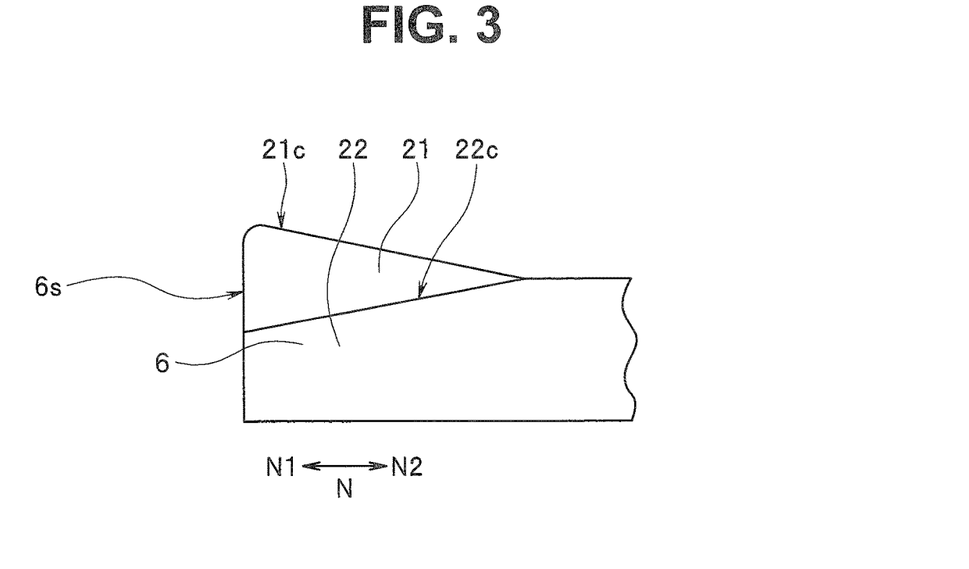
FIG. 3 is a side view of the distal end portion of FIG. 2 as viewed in a direction III in FIG. 2.
Figure 4:
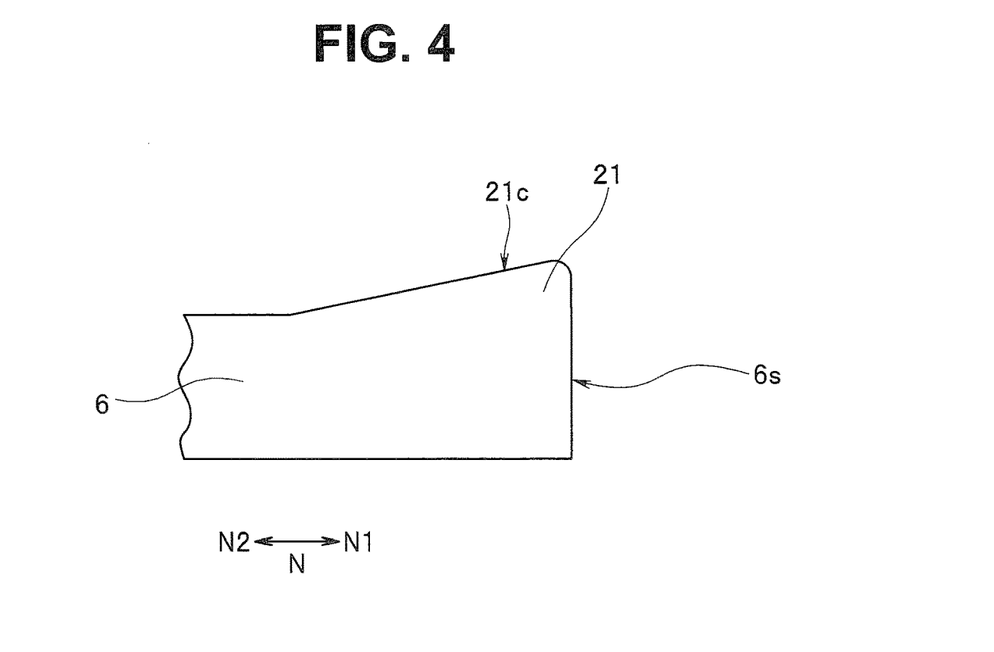
FIG. 4 is a side view of the distal end portion of FIG. 2 as viewed in a direction IV in FIG. 2.

Next, a configuration of the distal end portion 6 will be described with reference to FIGS. 2 to 4. FIG. 2 is an enlarged perspective view schematically viewing the distal end portion of the insertion portion of FIG. 1 in a direction II in FIG. 1. FIG. 3 is a side view of the distal end portion of FIG. 2 as viewed in a direction III in FIG. 2. FIG. 4 is a side view of the distal end portion of FIG. 2 as viewed in a direction IV in FIG. 2.

As shown in FIG. 2, a concave portion 20 with a predetermined length in the longitudinal axis direction N and a predetermined depth in a direction D is formed on a side surface 6i on part of a peripheral surface of the distal end portion 6, such as on a side surface 6i in the direction D substantially orthogonal to the longitudinal axis direction N.

The channel opening 25 of the treatment instrument insertion channel 19 opens on a bottom surface 20t of the concave portion 20.

The channel opening 25 has a planar shape extending in the longitudinal axis direction N that is one direction, such as a rectangular planar shape including opening edge portions 25c and 25d on a long side with a length x in the longitudinal axis direction N and including opening edge portions 25a and 25b on a short side with a length y (y<x) in a direction B substantially orthogonal to the longitudinal axis direction N and the direction D.

Note that the shape of the channel opening 25 is not limited to a rectangular shape as long as the channel opening 25 has a planar shape extending in one direction. In FIG. 2, to simplify the drawing, the treatment instrument raising base facing the channel opening 25 is not illustrated.

On the bottom surface 20t, an objective window 26 of an observation optical system provided in the distal end portion 6 for observing inside of the subject is arranged, and an illumination lens 27 for expanding and applying illumination light supplied from the light source apparatus 11 into the subject is arranged.

Note that a light emitting element, such as an LED, may be arranged on the bottom surface 20t in place of the illumination lens 27. The objective window 26 of the observation optical system is configured to be able to mainly observe a part positioned in a direction intersecting the longitudinal axis direction N, that is, on a lateral side of the distal end portion 6.

Note that the channel opening 25, the objective window 26, and the illumination lens 27 point to a lateral side of the longitudinal axis direction N, such as a direction D1 in the direction D.

Here, a pair of wall portions 21 and 22 extending in the longitudinal axis direction N are positioned on both ends in the direction B of the concave portion 20.

The pair of wall portions 21 and 22 are positioned to face each other across the channel opening 25, the objective window 26, and the illumination lens 27 in the direction B.

Note that although the pair of wall portions 21 and 22 are formed continuously with the side surface 6i in the longitudinal axis direction N in FIG. 2, the arrangement is not limited to this, and the pair of wall portions 21 and 22 may be formed discontinuously. In this case, the pair of wall portions 21 and 22 may extend longer than the concave portion 20 in the longitudinal axis direction N.

Respective end surfaces 21c and 22c of top portions of the pair of wall portions 21 and 22 point to the direction D1 just like the channel opening 25, the objective window 26, and the illumination lens 27 and extend in the longitudinal axis direction N.

The respective end surfaces 21c and 22c are inclined such that inclination directions are opposite to each other in the longitudinal axis direction N as shown in FIGS. 2 to 4.

More specifically, the end surface 21c of one wall portion 21 is inclined such that a diameter of the distal end portion 6 is enlarged from a proximal end side of the insertion portion 2 in the longitudinal axis direction N (hereinafter, simply called a proximal end side) toward the distal end side, that is, in a direction N1, that is, the end surface 21c ascends toward a distal end 6s of the distal end portion 6, as shown in FIGS. 2 and 4.

The end surface 22c of the other wall portion 22 is inclined such that the diameter of the distal end portion 6 is reduced in the direction N1 from the proximal end side of the insertion portion 2 in the longitudinal axis direction N, that is, the end surface 22c descends toward the distal end 6s, as shown in FIGS. 2 and 4.

Note that although not shown, the end surface 21c may be inclined to descend toward the distal end 6s, and the end surface 22c may be inclined to ascend toward the distal end 6s.

As shown in FIG. 2, the extension direction of each of the end surfaces 21c and 22c coincides with a direction of extension of the long side of the channel opening 25, that is, the longitudinal axis direction N.

Note that the shape of the inclination of each of the end surfaces 21c and 22c of the pair of wall portions 21 and 22 may be provided on a distal end rigid member not shown included in the distal end portion 6 or may be provided on a distal end cover covered by a periphery of the distal end rigid member.

That is, the pair of wall portions 21 and 22 may be provided on the distal end rigid member or may be provided on the distal end cover.

Figure 5:
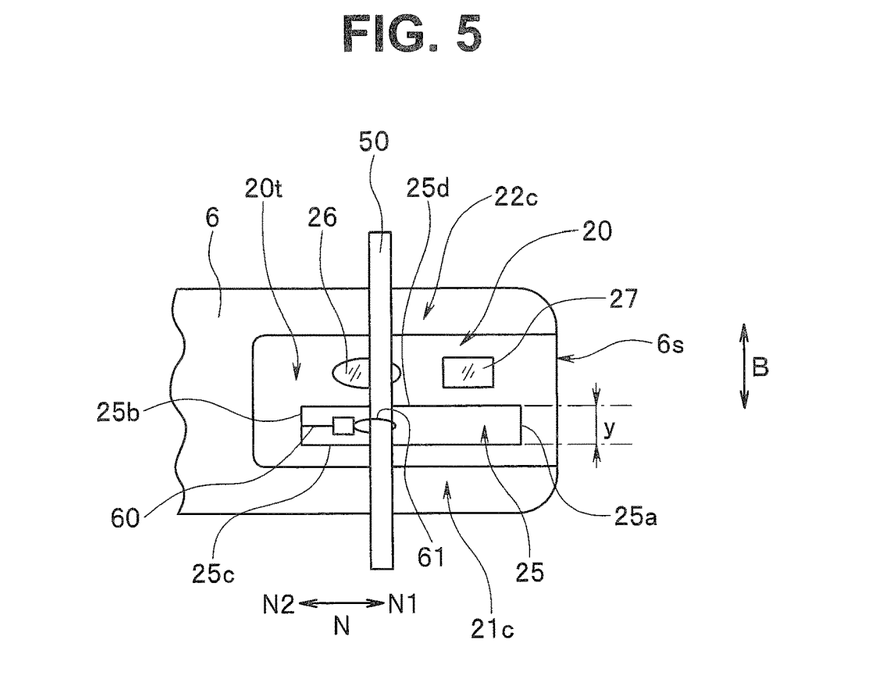
FIG. 5 is a plan view showing a state in which a stent is delivered across a channel opening in a direction having a short side of a channel opening and placed on a side surface of the distal end portion of FIG. 2.
Figure 6:
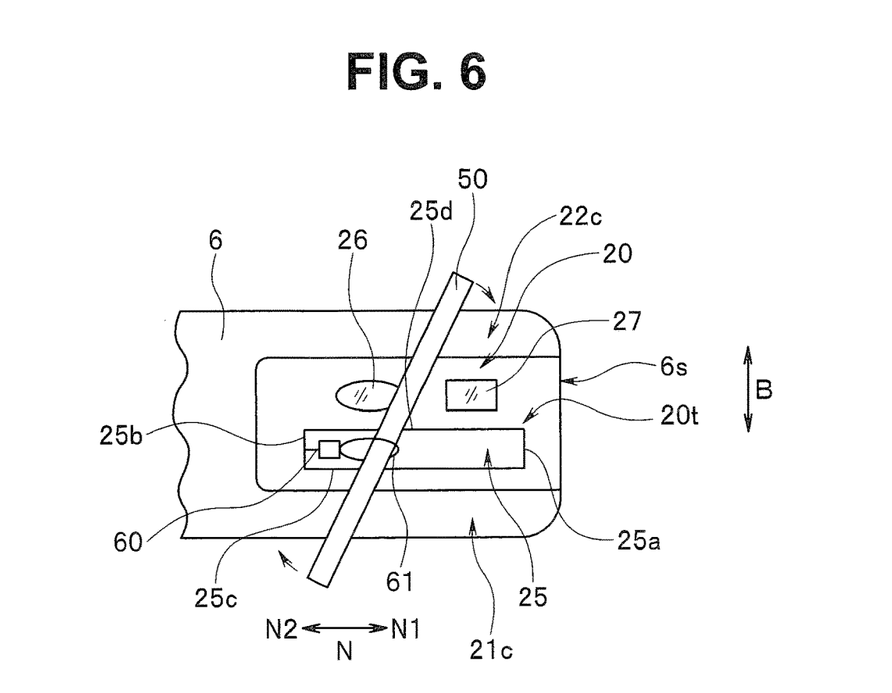
FIG. 6 is a plan view showing a state in which the stent of FIG. 5 is drawn toward the channel opening, and the stent is rotated along an inclined surface of each end surface of a pair of wall portions.
Figure 7:
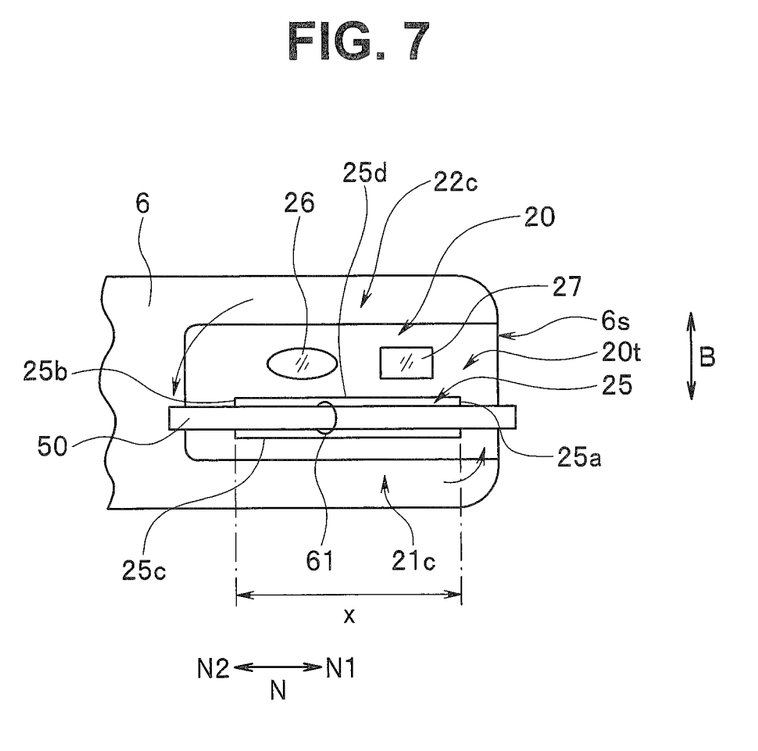
FIG. 7 is a plan view showing a state in which the stent of FIG. 6 is further drawn toward the channel opening to further rotate the stent, and the stent is delivered across the channel opening in a longitudinal axis direction.

Next, an effect of the present embodiment will be described with reference to FIGS. 5 to 9. FIG. 5 is a plan view showing a state in which a stent is delivered across a channel opening in a direction having the short side of the channel opening and placed on the side surface of the distal end portion of FIG. 2. FIG. 6 is a plan view showing a state in which the stent of FIG. 5 is drawn toward the channel opening, and the stent is rotated along the inclined surface of each end surface of the pair of wall portions. FIG. 7 is a plan view showing a state in which the stent of FIG. 6 is further drawn toward the channel opening to further rotate the stent, and the stent is delivered across the channel opening in the longitudinal axis direction.

Figure 8:
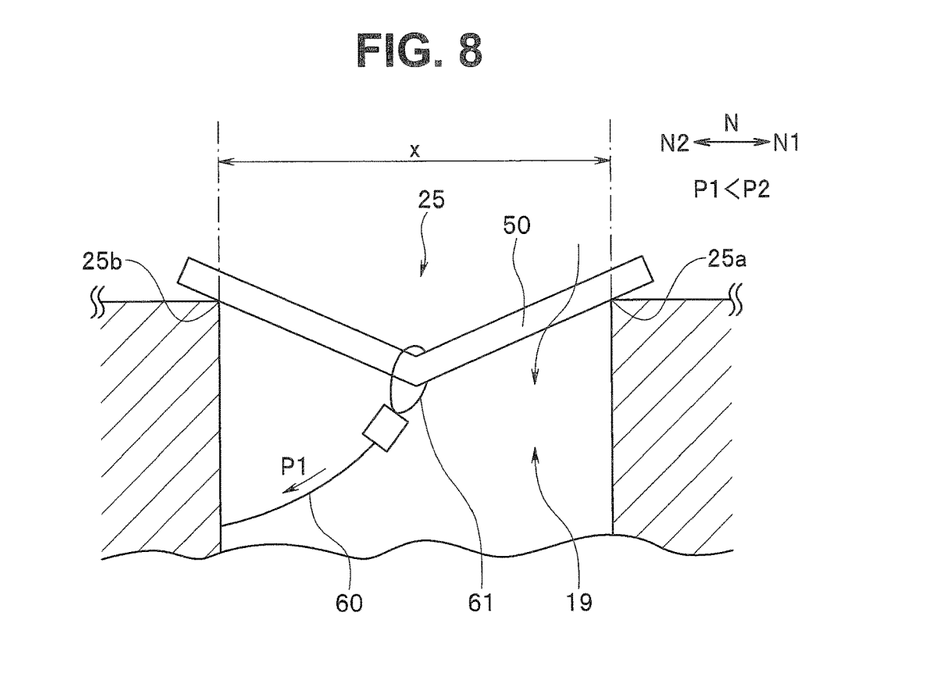
FIG. 8 is a partial cross-sectional view schematically showing a state in which the stent positioned in the longitudinal axis direction of FIG. 7 is further drawn toward the channel opening to fold the stent in half.
Figure 9:
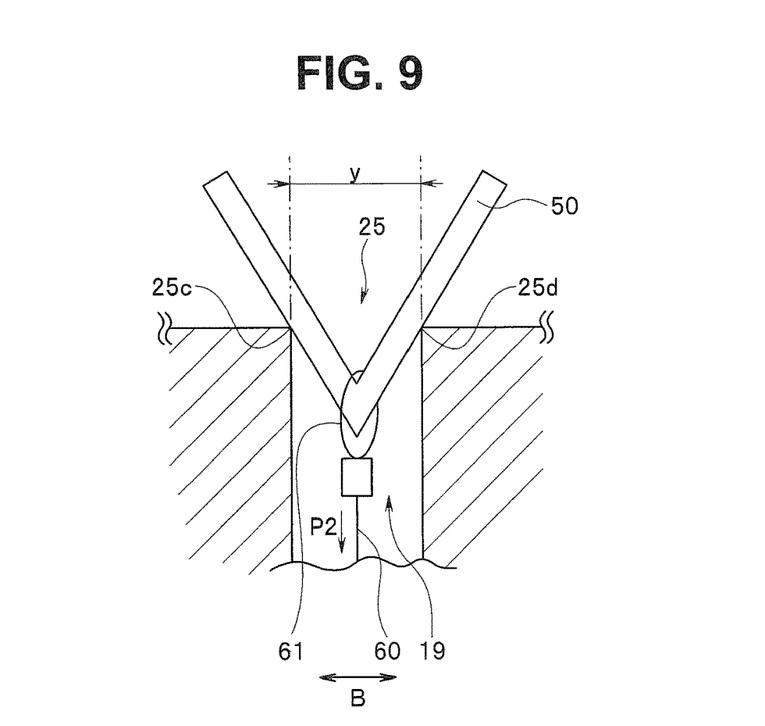
FIG. 9 is a partial cross-sectional view schematically showing a case in which the stent positioned in the direction having the short side of the channel opening of FIG. 5 is drawn toward the channel opening to fold the stent in half without rotating the stent.

FIG. 8 is a partial cross-sectional view schematically showing a state in which the stent positioned in the longitudinal axis direction of FIG. 7 is further drawn toward the channel opening to fold the stent in half. FIG. 9 is a partial cross-sectional view schematically showing a case in which the stent positioned in the direction having the short side of the channel opening of FIG. 5 is drawn toward the channel opening to fold the stent in half without rotating the stent.

To recover a stent 50 longer than the length x of the long side of the channel opening 25 placed in the subject, an operator first inserts the insertion portion 2 into the subject, up to a position that allows observation of the stent 50 through the objective window 26.

Next, the operator inserts the snare 60 into the treatment instrument insertion channel 19 through the treatment instrument insertion port 3e, until a loop portion 61 of the distal end of the snare 60 protrudes into the subject from the channel opening 25.

The operator then moves the insertion portion 2 back and forth, bends the bending portion 7 by operating the bending operation knob 3a, or raises and lowers the treatment instrument raising base not shown by operating the raising base operation knob 3d to adjust an angle of projection of the snare 60 placed on the treatment instrument raising base from the channel opening 25 on the distal end side or adjust the position of the snare 60 to insert the stent 50 into the loop portion 61. In this case, it is desirable to position the loop portion 61 substantially near the center of the elongated stent 50 in the extension direction.

Next, the operator draws the snare 60 toward a direction N2 in the longitudinal axis direction N to thereby draw the loop portion 61 toward the channel opening 25. As a result, the stent 50 held by the loop portion 61 also moves toward the channel opening 25, and as shown in FIG. 5, the stent 50 is delivered and placed between the respective end surfaces 21c and 22c of the pair of wall portions 21 and 22 across the channel opening 25 in the direction B.

Then, when the operator further draws the snare 60 toward the direction N2, the stent 50 starts to rotate clockwise as shown in FIG. 6 along the shapes of the descending inclinations of the respective end surfaces 21c and 22c, because the end surface 21c is inclined to descend toward the direction N2, and the end surface 22c is inclined to descend toward the direction N1. In this way, rotating the stent 50 clockwise also has an advantage of preventing the stent 50 from blocking the objective window 26 as shown in FIG. 6 when the stent 50 is rotated.

Particularly, when the objective window 26 is configured to observe the lateral side of the distal end portion 6, and the observation field of view is slightly inclined to the back side as in the present embodiment, the stent 50 moves outside or to an end of the observation field of view. This can prevent obstruction of the observation action as much as possible.

Note that as described above, when the end surface 21c is inclined to descend in the direction N1, and the end surface 22c is inclined to descend in the direction N2 (not shown), the stent 50 starts to rotate counterclockwise along the shapes of the descending inclinations of the respective end surfaces 21c and 22c. For example, if the position along the long axis N of the objective window 26 is further to the N1 side than in the configurations shown in FIGS. 5 and 6, the stent 50 moves outside or to the end of the observation field of view when the stent 50 is rotated counterclockwise.

The stent 50 can be more easily rotated if the pair of end surfaces 21c and 22c are shaped to further incline toward the channel opening 25 in the direction B.

Subsequently, when the operator further draws the snare 60 toward the direction N2, the stent 50 is positioned across the channel opening 25 in the longitudinal axis direction N as shown in FIG. 7, along the shapes of the descending inclinations of the respective end surfaces 21c and 22c.

Next, when the operator further draws the snare 60 toward the direction N2, the stent 50 is folded in half at the loop portion 61 while parts of the stent 50 come into contact with the opening edge portions 25a and 25b positioned in the direction B around the longitudinal axis direction N of the channel opening 25 as shown in FIG. 8.

Lastly, the operator further draws the snare 60 toward the direction N2 to draw the stent 50 folded in half into the treatment instrument insertion channel 19 along with the snare 60 and then recovers the stent 50 through the treatment instrument insertion port 3e.

Note that the reason that the inclinations of the respective end surfaces 21c and 22c are used to rotate the stent 50 up to the position across the channel opening 25 in the longitudinal axis direction N as shown in FIG. 7 is that the length x of the long side of the channel opening 25 is longer than the length y of the short side as shown in FIG. 2 (x>y). That is, the amount of delivery of the stent 50 with respect to the channel opening 25 is greater in FIG. 7 than in FIG. 5.

Therefore, an amount of drawing force P1 of the snare 60 for folding the stent 50 in half while bringing the parts of the stent 50 into contact with the opening edge portions 25a and

25*b* as shown in FIG. 8 in the state that the stent 50 is across the channel opening 25 in the longitudinal axis direction N as shown in FIG. 7 is smaller than an amount of drawing force P2 of the snare 60 for folding the stent 50 in half while bringing the parts of the stent 50 into contact with the opening edge portions 25*c* and 25*d* as shown in FIG. 9 in the state that the stent 50 is across the channel opening 25 in the direction B as shown in FIG. 5 (P1<P2). That is, the stent 50 can be folded in half with a smaller amount of force.

In this way, the present embodiment has illustrated that the inclination directions of the respective end surfaces 21*c* and 22*c* of the pair of wall portions 21 and 22 extending in the longitudinal axis direction N are opposite to each other in the longitudinal axis direction N at both end portions of the concave portion 20 in the direction B on the side surface 6*i* of the distal end portion 6.

According to this, when the snare 60 is used to draw the stent 50 into the treatment instrument insertion channel 19 through the channel opening 25, the shapes of the inclinations of the respective end surfaces 21*c* and 22*c* are used to fold the stent 50 in half as shown in FIG. 8 after rotating the stent 50 across the long side of the channel opening 25 in the longitudinal axis direction N as shown in FIG. 7.

In this case, the amount of drawing force P1 of the snare 60 for folding the stent 50 in half can be smaller than the amount of drawing force P2 of the snare 60 for folding the stent 50 in half as shown in FIG. 9 in the state that the stent 50 is across the short side of the channel opening 25 in the direction B as shown in FIG. 5 (P1<P2).

Note that the matter to be recovered is not limited to the stent 50, and the same applies to other elongated matters, and the same also applies to other recovery treatment instruments such as grasping forceps.

As described, the simple configuration of only providing the inclined surfaces in opposite inclination directions on the respective end surfaces 21*c* and 22*c* of the pair of wall portions 21 and 22 on the side surface 6*i* of the distal end portion 6 can provide a distal end structure of an endoscope with a configuration that allows easily folding in half an elongated matter to be recovered in the subject to recover the matter to be recovered through the channel opening 25 by using a recovery treatment instrument.

Figure 10:
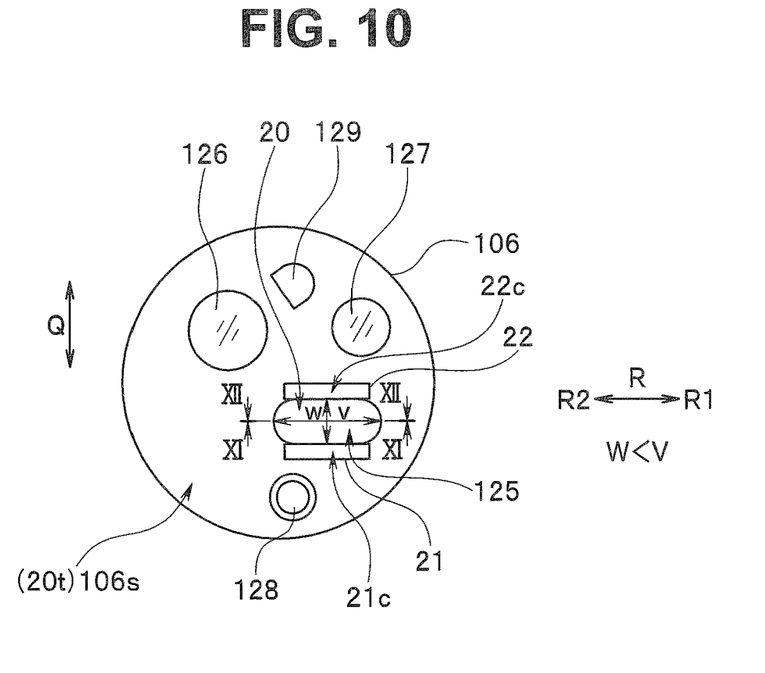
FIG. 10 is a plan view showing a distal end surface of a distal end portion of a front-view type endoscope.
Figure 11:
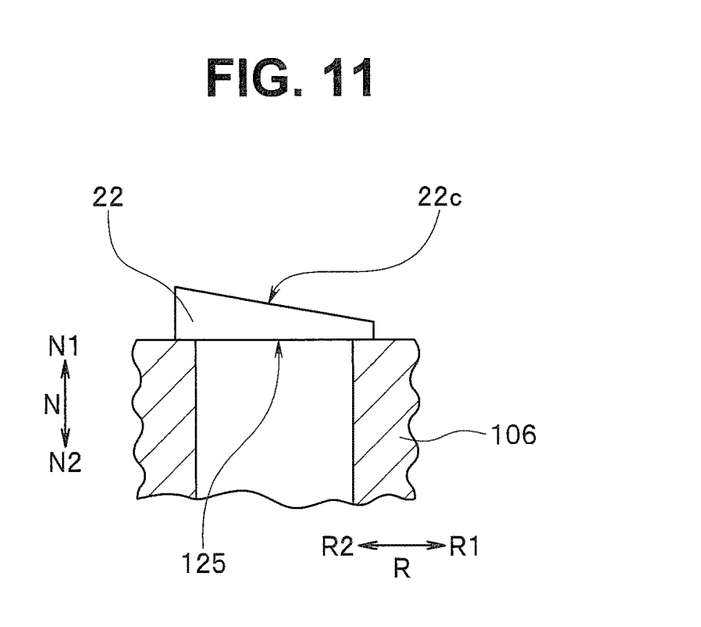
FIG. 11 is a partial cross-sectional view illustrating the distal end portion of FIG. 10 along a line XI-XI in FIG. 10.
Figure 12:
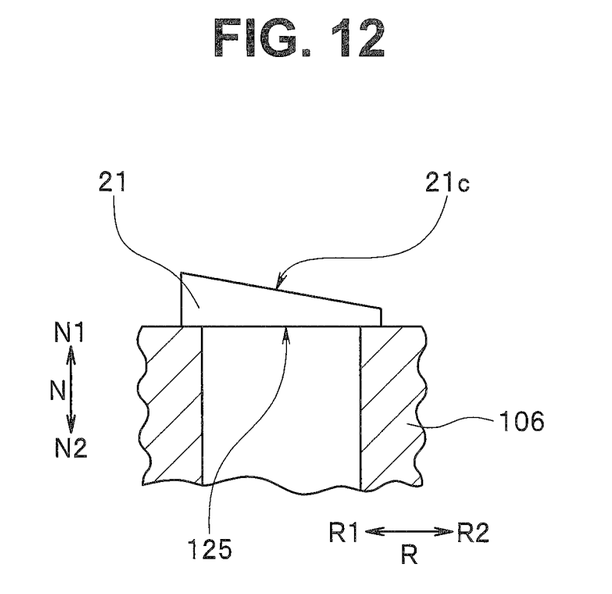
FIG. 12 is a partial cross-sectional view illustrating the distal end portion of FIG. 10 along a line XII-XII in FIG. 10.

Note that a modification will be illustrated below with reference to FIGS. 10 to 12. FIG. 10 is a plan view showing a distal end surface of a distal end portion of a front-view type endoscope. FIG. 11 is a partial cross-sectional view illustrating the distal end portion of FIG. 10 along a line XI-XI in FIG. 10. FIG. 12 is a partial cross-sectional view illustrating the distal end portion of FIG. 10 along a line XII-XII in FIG. 10.

The endoscope is a side-view type endoscope in the example illustrated in the present embodiment described above. The endoscope is not limited to this, and as shown in FIG. 10, the present embodiment can also be applied to the distal end structure of the front-view type endoscope.

More specifically, as shown in FIG. 10, an objective window 126, an illumination lens 127, a front water feeding nozzle 128, and an air/water feeding nozzle 129 for supplying fluid to the objective window 126 are provided on a distal end surface 106*s* of a distal end portion 106 of the insertion portion of the endoscope. Note that the illumination lens 127 may be a light emitting element such as an LED.

Furthermore, a channel opening 125 of the treatment instrument insertion channel 19 opens on the distal end surface 106*s*.

The channel opening 125 has a planar shape extending in one direction R in the radial direction of the distal end portion 6, such as an elliptical planar shape having a long side with a length v in the one direction R and a short side with a length w in another direction Q substantially orthogonal to the one direction R in the radial direction of the distal end portion 6 (w<v).

Note that the shape of the channel opening 125 is not limited to the elliptical shape as long as the channel opening 125 has a planar shape extending in one direction. The treatment instrument raising base facing the channel opening 125 is not illustrated in FIG. 10, either, to simplify the drawing. Note that as shown in FIG. 10, it is obvious that the treatment instrument raising base may not be provided in the front-view type endoscope.

The pair of wall portions 21 and 22 sandwiching the channel opening 125 in the other direction Q and extending in the one direction R are provided on the distal end surface 106*s*.

Note that the pair of wall portions 21 and 22 form the concave portion 20 between the wall portion 21 and the wall portion 22 in the other direction Q. That is, the bottom surface 20*t* of the concave portion 20 is faulted at a site of the distal end surface 106*s* placed between the wall portion 21 and the wall portion 22 in the other direction Q, and the channel opening 125 opens on the bottom surface 20*t*.

The respective end surfaces 21*c* and 22*c* of the top portions of the pair of wall portions 21 and 22 extend in the one direction R.

The respective end surfaces 21*c* and 22*c* are inclined in the one direction R such that the inclination directions are opposite to each other as shown in FIGS. 11 and 12.

More specifically, the end surface 21*c* of one wall portion 21 is inclined to descend from a direction R1 to a direction R2 in the one direction R as shown in FIG. 12.

The end surface 22*c* of the other wall portion 22 is inclined to descend from the direction R2 to the direction R1 in the one direction R as shown in FIG. 11.

Note that as in the present embodiment, the end surface 21*c* may be inclined to descend from the direction R2 to the direction R1 in the one direction R, and the end surface 22*c* may be inclined to descend from the direction R1 to the direction R2 in the one direction R.

As shown in FIG. 10, the extension direction of each of the end surfaces 21*c* and 22*c* coincides with the direction of extension of the long side of the channel opening 125, that is, the one direction R.

Note that the shape of the inclination of each of the end surfaces 21*c* and 22*c* of the pair of wall portions 21 and 22 may be provided on the distal end rigid member not shown included in the distal end portion 6 or may be provided on the distal end cover covered by the periphery of the distal end rigid member.

That is, the pair of wall portions 21 and 22 may be provided on the distal end rigid member or may be provided on the distal end cover.

Next, an effect of the configuration of FIGS. 10 to 12 will be described.

To recover the stent 50 longer than the length v of the long side of the channel opening 125 placed in the subject, the operator first inserts the insertion portion 2 into the subject up to a position that allows observation of the stent 50 through the objective window 126.

Next, the operator inserts the snare 60 into the treatment instrument insertion channel 19 through the treatment instrument insertion port 3e, until the loop portion 61 of the distal end of the snare 60 protrudes into the subject from the channel opening 125.

The operator then moves the insertion portion 2 back and forth or bends the bending portion 7 by operating the bending operation knob 3a to insert the stent 50 into the loop portion 61. In this case, the loop portion 61 is positioned substantially near the center of the elongated stent 50 in the extension direction.

Next, the operator draws the snare 60 toward the direction N2 in the longitudinal axis direction N to thereby draw the loop portion 61 toward the channel opening 125. As a result, the stent 50 held by the loop portion 61 also moves toward the channel opening 125, and the stent 50 is delivered and placed on the respective end surfaces 21c and 22c of the pair of wall portions 21 and 22 across the channel opening 25 in the other direction Q.

Then, when the operator further draws the snare 60 toward the direction N2, the stent 50 starts to rotate clockwise along the shapes of the descending inclinations of the respective end surfaces 21c and 22c, because the end surface 21c is inclined to descend toward the direction R2, and the end surface 22c is inclined to descend toward the direction R1.

Note that as described above, when the end surface 21c is inclined to descend in the direction R1, and the end surface 22c is inclined to descend in the direction R2, the stent 50 starts to rotate counterclockwise along the shapes of the descending inclinations of the respective end surfaces 21c and 22c.

The stent 50 can be more easily rotated if the pair of end surfaces 21c and 22c are shaped to further incline toward the channel opening 125 in the other direction Q.

Subsequently, when the operator further draws the snare 60 toward the direction N2, the stent 50 is positioned across the channel opening 25 in the one direction R, along the shapes of the descending inclinations of the respective end surfaces 21c and 22c.

Next, when the operator further draws the snare 60 toward the direction N2, the stent 50 is folded in half at the loop portion 61 while parts of the stent 50 come into contact with opening edge portions of the channel opening 125.

Lastly, the operator further draws the snare 60 toward the direction N2 to draw the stent 50 folded in half into the treatment instrument insertion channel 19 along with the snare 60 and then recovers the stent 50 through the treatment instrument insertion port 3e.

In this way, the same advantageous effect as in the present embodiment described above can also be obtained when the present embodiment is applied to the distal end structure of the front-view type endoscope.

What is claimed is:

1. A distal end structure of an endoscope, the distal end structure comprising:
   an opening of a treatment instrument insertion channel formed on a distal end of an insertion portion in the endoscope and including an opening having a long side and a short side, the long side having a length greater than a length of the short side;
   a first wall extending in a direction parallel to the long side, the first wall being disposed at the distal end of the insertion portion; and
   a second wall facing the first wall in a direction parallel to the short side and extending in a direction parallel to the long side direction such that the first and second walls sandwich the opening, the second wall being disposed at the distal end of the insertion portion, wherein
   a first end surface of a top portion on the first wall and a second end surface of a top portion on the second wall are inclined such that a first inclination direction of the first end surface and a second inclination direction of the second end surface in the direction parallel to the long side are opposite to each other.

2. The distal end structure according to claim 1, wherein the opening is formed on a side surface of the distal end of the insertion portion, the direction parallel to the long side coincides with a longitudinal axis direction of the insertion portion, and
   the first end surface and the second end surface point to a lateral side with respect to the longitudinal axis direction.

3. The distal end structure according to claim 2, further comprising:
   an objective window of an observation optical system configured to observe inside of a subject arranged on the side surface of the distal end of the insertion portion,
   wherein the first end surface and the second end surface face each other across the opening and the objective window.

4. The distal end structure according to claim 2, further comprising:
   an objective window of an observation optical system configured to observe inside of a subject arranged on the side surface of the distal end of the insertion portion,
   the first end surface and the second end surface face each other across the opening and the objective window, the first wall is arranged close to the objective window, and the second wall is arranged close to the opening.

5. The distal end structure according to claim 2, wherein the first end surface and the second end surface extend in the longitudinal axis direction.

6. The distal end structure according to claim 5, wherein the first inclination direction is inclined in a direction in which a diameter of the insertion portion is enlarged from a proximal end side toward a distal end side of the insertion portion in the longitudinal axis direction, and
   the second inclination direction is inclined in a direction in which the diameter of the insertion portion is reduced from the proximal end side toward the distal end side of the insertion portion in the longitudinal axis direction.

7. The distal end structure according to claim 5, wherein the first inclination direction is inclined in a direction in which a diameter of the insertion portion is reduced from a proximal end side toward a distal end side of the insertion portion in the longitudinal axis direction, and
   the second inclination direction is inclined in a direction in which the diameter of the insertion portion is enlarged from the proximal end side toward the distal end side of the insertion portion in the longitudinal axis direction.

8. The distal end structure according to claim 3, wherein the first end surface and the second end surface extend in the longitudinal axis direction,
   the first inclination direction is inclined in a direction in which a diameter of the insertion portion is reduced from a proximal end side toward a distal end side of the insertion portion in the longitudinal axis direction, and the second inclination direction is inclined in a direction in which the diameter of the insertion portion is enlarged from the proximal end side toward the distal end side of the insertion portion in the longitudinal axis direction.

9. The distal end structure according to claim 3, wherein the first end surface and the second end surface extend in the longitudinal axis direction, the second inclination direction is inclined in a direction in which a diameter of the insertion portion is reduced from a proximal end side toward a distal end side of the insertion portion in the longitudinal axis direction, and the first inclination direction is inclined in a direction in which the diameter of the insertion portion is enlarged from the proximal end side toward the distal end side of the insertion portion in the longitudinal axis direction.

\* \* \* \* \*